United States Patent [19]

Feld

[11] Patent Number: 4,490,298

[45] Date of Patent: Dec. 25, 1984

[54] METHOD OF ISOLATING COBALT AND/OR MANGANESE AS OXALATES

[75] Inventor: Marcel Feld, Cologne, Fed. Rep. of Germany

[73] Assignee: Dynamit Nobel AG, Cologne, Fed. Rep. of Germany

[21] Appl. No.: 462,862

[22] Filed: Feb. 1, 1983

[30] Foreign Application Priority Data

Feb. 10, 1982 [DE] Fed. Rep. of Germany ....... 3204510

[51] Int. Cl.$^3$ .................. C07F 11/00; C07F 15/06
[52] U.S. Cl. .................. 260/429 R; 260/439 R; 562/412; 562/414; 562/493; 502/152
[58] Field of Search ................. 562/412, 414, 493; 260/429 R, 439 R; 252/413

[56] References Cited

U.S. PATENT DOCUMENTS

| | | | |
|---|---|---|---|
| 3,332,971 | 7/1967 | Elder et al. | 260/439 R |
| 3,803,191 | 4/1974 | Ehrreich et al. | 260/439 R |
| 3,840,469 | 10/1974 | Hobbs et al. | 260/439 R X |
| 4,170,602 | 10/1979 | Deffeyes et al. | 260/439 R |
| 4,314,073 | 2/1982 | Crooks | 562/412 X |
| 4,329,493 | 5/1982 | Hashizume et al. | 562/414 |
| 4,346,230 | 8/1982 | Hoffman et al. | 562/412 |

*Primary Examiner*—Helen M. S. Sneed
*Attorney, Agent, or Firm*—Felfe & Lynch

[57] ABSTRACT

In a process for the isolation of cobalt and/or manganese in the form of precipitated, easily filtrable cobalt and/or manganese oxalates from acetic acid solutions or extracts, the solutions in question are treated with oxalic acid dimethyl or diethyl ester at temperatures of 50° to 250° C.

14 Claims, No Drawings

METHOD OF ISOLATING COBALT AND/OR MANGANESE AS OXALATES

BACKGROUND OF THE INVENTION

The present invention concerns a method for the isolation of cobalt and/or manganese in the form of precipitated, easily filtrable cobalt and/or manganese oxalates from solutions of cobalt and/or manganese compounds, in addition, in some cases, to other heavy metal compounds and organic and/or inorganic substances, in aliphatic carboxylic acids or water or in mixtures thereof.

The present method is especially suitable for the isolation of cobalt and/or manganese salts from acetic acid oxidation mother liquors in which they have served as catalysts in the oxidation of alkyl aromatics with atmospheric oxygen in acetic acid solution for the preparation of aromatic carboxylic acids. Such oxidation processes are of great economic inportance. This is especially true of the production of terephthalic acid by the oxidation of p-xylene. Similar methods, however, are used in preparing other mononuclear or polynuclear aromatic mono-, di- or polycarboxylic acids, such as for example chlorobenzoic or nitrobenzoic acid, isophthalic acid, naphthalic dicarboxylic acid, trimellitic acid etc.

An important factor in the economy of such processes is the recovery of the catalyst. In most of the methods described for the recovery of catalyst from oxidation mother liquors, such as the one described, for example, in DE-OS No. 2,131,470, DE-OS No. 2,419,323 or DE-OS No. 2,260,491, the catalysts are isolated as carbonates. For this purpose, however, the acetic acid solutions must first be concentrated and the residues extracted with water. The extraction of this often tarry, and occasionally even 2-phase residue, is problematic and not always sufficiently effective. An incomplete extraction of the cobalt, however, signifies not only losses of the relatively expensive catalyst, but also makes it appreciably more difficult to get rid of the residual product which then still contains cobalt.

A method for the recovery of cobalt and/or manganese catalyst from acetic acid oxidation mother liquors is described in Japanese OS No. 97593/76. In this case the heavy metal catalyst in the oxidation mother liquor is precipitated in the form of a difficultly soluble oxalate by the addition of oxalic acid, and isolated by a solid-from-liquid separating method. This process offers the possibility of separating other heavy metal oxalates precipitated together with the cobalt and/or manganese oxalate by washing them out.

When the method of the Japanese patent application was attempted, the cobalt oxalate precipitated from acetic acid oxidation mother liquors or from acetic acid solutions of cobalt acetate proved to be virtually unfiltrable. Even when the precipitation conditions were varied as regards temperature, degree of aqueous dilution of the solution, cobalt concentration or method of adding the oxalic acid, easy filtrability could not be achieved. The addition of filter aids brought no improvement. In all cases the cobalt and/or manganese oxalate was obtained in a form in which it was virtually unfiltrable by means of filtration centrifuges, or suction or pressure filters.

Examination with the scanning electron microscope of the cobalt oxalate obtained in Prior-Art Example 1 revealed the reason for the extraordinary difficulty encountered in filtration: the crystallizate consisted of small, rounded primary particles with a diameter of only about 0.1 to 0.3 microns. It is thus apparent that the filtration of this extremely finely crystalline product with conventional filtration apparatus was incomplete and could be accomplished only in a very time-consuming manner, even using a disproportionately large filtration surface area. In the case of relatively great layer thicknesses, filtration was completely impossible, since then the small, rounded crystals were packed together into a very dense layer blocking the flow of liquid.

THE INVENTION

It is the object of the invention to obtain a considerably more coarsely crystalline, relatively easily filtrable cobalt and/or manganese oxalate.

This object is achieved by the invention. It consists in a method of the kind described above, which is characterized in that the solutions are treated with oxalic esters at elevated temperatures of 50° to 250° C., the cobalt and/or manganese oxalate is isolated by solid-from-liquid separation methods, and freed of any other precipitated heavy metal oxalates by washing with water in a manner known in itself.

In accordance with the invention, it is not oxalic acid that is used for the precipitation, but instead the solution of cobalt and/or manganese salts is treated at elevated temperature with esters of oxalic acid such as, for example, oxalic acid dimethyl ester or oxalic acid diethyl ester. Under these conditions the cobalt oxalate forms gradually, but reaction times of, for example, less than one hour under refluxing conditions may suffice for a quantitative precipitation of the heavy metals, such precipitation of the heavy metals from acetic acid solution being considered to be quantitative when the concentration in the solution falls to less than 1 ppm.

The scanning electron microscopic examination of the cobalt oxalate obtained by two hours of refluxing with the use of oxalic acid ester prepared from 95% acetic acid reveals cubic crystals which have intergrown to form clusters of a predominant magnitude of 4 to 10 microns. The extremely good filtrability of these bizarre-shaped and greatly intergrown crystals is easy to understand. The crystal clusters are not agglomerates, because they are not broken up by ultrasound treatment. The crystal clusters are therefore mechanically strong, and the easy filtration characteristics remain unchanged even under technical processing conditions.

Equally important to a quantitative precipitation of the dissolved heavy metal within reasonable lengths of time is a sufficient water content in the solution. Insoluble cobalt oxalate forms also when a virtually water-free solution of cobalt salts in acetic acid is treated with esters of oxalic acid, but then the precipitation of the cobalt is not quantitative, even after more than 10 hours of reaction. A comparison of Examples 2, 3, 4 and 5 of the invention will show the positive effect of water on the speed with which quantitative precipitation is accomplished.

For the precipitation of cobalt and/or manganese oxalate from acetic acid solutions of these heavy metals, therefore, a water content in the solution of more than 1% by weight, preferably more than 2%, and especially 5 to 10%, is considered to be desirable. There is no upper limit, however, to the degree of aqueous dilution. Ultimately, the process can be extended also to aqueous solutions of cobalt and/or manganese salts containing no acetic acid. Cobalt precipitation from an aqueous solution is, however, not as good as from acetic acid solutions, since then the residual cobalt content remaining in solution is approximately 30 to 50 ppm.

On account of the possibility of isolating cobalt and/or manganese as easily filtrable oxalates from aqueous solutions of cobalt and/or manganese salts, the process is not limited to the recovery of cobalt and/or manganese used as catalyst in oxidation processes performed in acetic acid solution. Indeed, the process can also serve for the recovery of these heavy metals from other processes, such as for example oxidation processes performed in media containing no acetic acid, or carbonylation or hydrocarboxylation processes if the cobalt and/or manganese can be brought into an acetic acid or aqueous solution in these processes, for example by the extraction of distillation residues.

The time required for a quantitative precipitation of cobalt and/or manganese by the method of the invention depends not only on the water content of the solution but also on the temperature, the concentration of the cobalt and/or manganese, and the amount of oxalic ester used in relation thereto. An increasing excess of the oxalic ester produces an especially positive result, while at the same time the shorter reaction times thus achieved do not substantially affect the filtration properties of the precipitated cobalt and/or manganese oxalate.

At least an equimolecular amount of oxalic ester is necessary for a quantitative precipitation of the cobalt and/or manganese. To achieve reasonably practical reaction times of less than 6 hours, the oxalic ester will nevertheless be used in an excess of as much as four times the theoretically required molecular amount, but preferably 0.1 to 0.5 times the theoretically required amount. At the same time, the precipitation is performed at an elevated temperature of 50° to 250° C., preferably 80° to 160° C.

Basically, the quantitative precipitation of cobalt and/or manganese by the method of the invention can be accelerated by the addition of strong acids, such as mineral acids, for example. In general, however, the measures stated previously will suffice to achieve a complete precipitation of the heavy metal in the form of an easily filtrable crystallizate in reasonable periods of time.

The isolation of the cobalt and/or manganese oxalate obtained in especially easily filtrable form by the present method can be performed with the use of conventional filtration apparatus, such as pressure filters or filter centrifuges, for example. The filtration can be performed either at room temperature or at higher temperatures.

The isolation of the heavy metal oxalate at an elevated temperature of, for example, 80° to 110° C. can be advantageous for the preparation of a product that is relatively easily soluble in heated acetic acid. If, for example, the oxidation product that crystallizes out upon cooling to room temperature is discolored by the catalyst and can be purified only with an appreciable reduction of the yield by thorough washing or by recrystallization, the precipitation and separation of the heavy metal oxalate can advantageously be performed while the reaction mixture is hot, prior to the isolation of the target product.

It has already been mentioned that the method of the invention is not limited to the isolation of cobalt and/or manganese from the acetic acid mother liquors resulting from processes for the preparation of aromatic carboxylic acids by the oxidation of alkyl aromatics with oxygen in an acetic acid solution, although it is very suitable for that purpose. An additional application that is also very attractive from the economic point of view is the recovery of catalyst by the combined air oxidation in the liquid phase of p-xylene and p-toluylic acid methyl ester, esterification of the oxidate with methanol and separation of the esterification mixture by distillation (cf. Hydrocarbon Processing, Nov. 1981, p. 151). In this multiple-step process, cobalt salts or cobalt and manganese salts are used as oxidation catalysts, but the oxidation is performed in an acetic acid-free medium. The catalyst is isolated by extraction from the distillation residues containing cobalt or both cobalt and manganese. A very appropriate extractant is acetic acid. However, other organic and inorganic byproducts get into the extract in addition to the cobalt or the cobalt and manganese, and some of them interfere with the oxidation. Therefore, an acetic acid extract of distillation residues that contains cobalt, or cobalt and manganese together, cannot be recycled directly into the oxidation process to serve as a catalyst-containing solution, and instead the valuable catalysts have to be re-isolated from such extracts by an appropriate method. The method of the invention can be used in this case, since it offers the possibility of freeing the catalyst, precipitated in the form of an easily filtrable oxalate, from organic and inorganic impurities simply by washing. The oxalate purified in this manner can then be transformed by known methods to a compound suitable for use as catalyst.

Also in the case of the isolation of cobalt and/or manganese compounds by oxalate precipitation by the method of the invention, from the distillation residue dissolved with acetic acid or another aliphatic carboxylic acid, the filtration at elevated temperature of the heavy metal oxalate may be necessary if the distillation residue is one that is soluble in the carboxylic acid only at elevated temperature.

If, in addition to cobalt, an aliphatic carboxylic acid contains as impurities dissolved components of high-grade steel, i.e., iron, chromium and nickel which have entered the solution by corrosion, these are precipitated together with the cobalt by using a sufficient excess of oxalic ester when applying the method of the invention. The cobalt oxalate removed by filtration can be freed of these impurities in a known manner by washing with water. On the other hand, however, it is also possible to precipitate the cobalt with surprisingly high selectivity and keep the rest of the heavy metals in solution, by avoiding a great excess of oxalic acid, and interrupting the reaction immediately after the quantitative precipitation of the cobalt by cooling the suspension to room temperature.

The method of the invention for the precipitation of cobalt or manganese oxalate in an especially easily filtrable form will be further explained by the examples described hereinbelow. Unless otherwise stated in these examples, the solid-from-liquid separations are always performed under the same conditions with the same vacuum filtration apparatus, using filters of a diameter of 27 mm, of a filtration time being from 6 to 12 seconds in accordance with DIN 53137. The filtration times stated in the examples also include the washing. The mother liquors were tested for their residual content of cobalt(II) ions with $Co^{2+}$ test bars.

EXAMPLES

Examples 1 to 9

A solution of 2.1 g of cobalt acetate tetrahydrate in 100 g of acetic acid (Examples 1 to 7) and in 100 g of water (Examples 8 and 9) was refluxed after the addition of oxalic acid diethyl ester until the cobalt content of the solution fell to less than 1 ppm (Examples 1 to 7) and to less than 50 ppm (Examples 8 and 9). The suspension was cooled to room temperature, filtered under the conditions described above, and the filter cake was washed successively with 10 g of acetic acid and water (Examples 1 to 7) and with only 10 g of water (Examples 8 and 9). The table gives the water content of the acetic acid used in Examples 1 to 7, stated in percentages by weight, the amount of the oxalic acid diethyl ester in grams and in mol-% with respect to the cobalt content of the solution, and the reaction time and filtration time in minutes.

| Example | Water content wt % | Oxalic acid diethyl ester g | Oxalic acid diethyl ester mole % | Reaction time, in minutes | Filtration time, in minutes |
|---|---|---|---|---|---|
| 1 | 5 | 3.4 | 280 | 55 | about 0.5 |
| 2 | 2 | 1.6 | 130 | 330 | about 0.5 |
| 3 | 5 | 1.6 | 130 | 300 | less than 1 |
| 4 | 10 | 1.6 | 130 | 135 | less than 1 |
| 5 | 50 | 1.6 | 130 | 90 | about 0.5 |
| 6 | 5 | 3.7 | 300 | 120 | less than 1 |
| 7 | 10 | 3.7 | 300 | 40 | less than 1 |
| 8 | 100 | 2.0 | 160 | 120 | less than 1 |
| 9 | 100 | 1.3 | 100 | 180 | less than 1 |

In Example 3, the solution still had a cobalt content of about 30 ppm after 4 hours. In Example 6, after 40 minutes a cobalt content of about 200 ppm could still be measured.

Example 10

The experiment described in Example 3 was repeated using 1.3 g of oxalic acid dimethyl ester (130 mol-% with respect to the cobalt content) instead of the oxalic acid diethyl ester used in that example. The precipitation of the cobalt was quantitative after a reaction time of 4.5 hours, the residual cobalt content of the mother liquor being less than 1 ppm. The filtration time was about 3 minutes.

Example 11

Example 10 was repeated with 1.6 g of oxalic acid dimethyl ester. The cobalt precipitation was completed after less than 2 hours, the filtration time was about 1 minute.

Example 12

The experiment described in Example 4 was repeated with a solution of 2.1 g of manganese(II) acetate tetrahydrate in 100 g of 90% acetic acid. The white crystallizate that formed was suction filtered with a filtration time of less than 1 minute, washed and dried. Yield: 1.4 g.

Example 13

600 g of a mother liquor with a water content of 1.0 wt.-% and a heavy metal content of 0.43 wt.-% Co, 0.09 wt.-% Fe, 0.03 wt.-% Cr, 0.02 wt.-% Ni and 24 ppm Mn, which was the reaction medium remaining after frequent reuse in the preparation of p-nitrobenzoic acid by the oxidation of p-nitrotoluene with atmospheric oxygen in an acetic acid solution, catalyzed by cobalt salts and bromides, and after the target product as well as most of the reaction water had been separated, was treated with 35 g of water and 7.4 g of oxalic acid diethyl ester (110 mol-% with respect to the cobalt content) and refluxed with stirring. After three hours the cobalt content of the solution had diminished to less than 100 ppm, and after four hours no more cobalt could be definitely detected in the solution with $Co^{2+}$ test bars, the limit of detectability being approximately 10 ppm in the colored mother liquor. The suspension, cooled to room temperature, was filtered through a pressure filter within less than two minutes at a forepressure of less than three bar. A content of 0.11 wt.-% Fe and 0.03 wt.-% Cr plus 11 ppm of Co was detected in the mother liquor. The filter cake, after being washed with 20 g of acetic acid followed by three washings with 20 g of water, and dried, yielded 8.1 g of cobalt(II) oxalate dihydrate with a cobalt content of 32.2 wt.-% (same as the theory). The colorless aqueous washing filtrate concentrated to the dry yielded a residue of less than 0.1 g.

Example 14

The experiment described in Example 13 was repeated with 11.2 g of oxalic acid diethyl ester (170 mol-% with respect to the cobalt content). After only 135 minutes of reaction time no more cobalt could be detected in the solution with $Co^{2+}$ test bars. 8.1 g of cobalt oxalate dihydrate was recovered by pressure filtration. The acetic acid mother liquor obtained after the filtration contained in this case only 0.04 wt.-% Fe, less than 0.02% Cr and 5 ppm of Co. The very dark-colored aqueous washing filtrate yielded this time a residue from concentration by evaporation of 2.9 g containing 17 wt.-% Fe and 1.8 wt.-% Cr.

Example 15

200 g of a distillation residue from the preparation of dimethyl terephthalate by the method described in Hydrocarbon Processing, Nov. 1981, p. 151, and containing 0.45 wt.-% of cobalt and 0.08 wt.-% of manganese, was dissolved with heating in 500 g of acetic acid; the solution was treated with 18 g of water and 5 g of oxalic acid diethyl ester, and refluxed for 6 hours with stirring. The suspension, cooled to room temperature, was filtered through a pressure filter (filtration time less than 3 minutes), the filter cake was washed twice with 20 g of acetic acid and water each time, and dried. The product was 3.3 g of a mixture of cobalt oxalate and manganese oxalate with a cobalt content of 27 wt.-% and a manganese content of 5 wt.-%.

Prior-Art Example 1

A solution of 2.1 g of cobalt acetate tetrahydrate in 100 g of a 93% acetic acid by weight was treated with 1.3 g of oxalic acid at room temperature with stirring, and then stirring was continued for one hour. The suspension proved to be unfiltrable under the filtration conditions of Examples 1 to 12: the filtrate initially obtained was very turbid, while the rate of filtration diminished rapidly, until finally the passage of the liquid through the filter was completely blocked for more than half of the total suspension.

Prior-Art Example 2

The experiment described in Prior-Art Example 1 was repeated with 1.4 g of oxalic acid, but after the addition of the oxalic acid, the solution was refluxed with stirring. After three hours the solution still had a cobalt content of greater than 300 ppm. As the reaction progressed, the reaction mixture became steadily more pasty and more and more inclined to delay in boiling. The filtration properties were then the same as in the preceding experiment.

It will be understood that the specification and examples are illustrative but not limitative of the present invention and that other embodiments within the spirit and scope of the invention will suggest themselves to those skilled in the art.

What is claimed is:

1. A process for the recovery of cobalt and/or manganese in the form of precipitated, easily filtrable cobalt and/or manganese oxalates from solutions of cobalt and/or manganese compounds in aliphatic carboxylic acids, water or mixtures thereof and which may contain other heavy metal compounds, inorganic and organic substances, comprising mixing the solutions with oxalic esters at temperatures from about 50° to 250° C. and separating the cobalt and/or manganese oxalate by a solid-from-liquid separation method.

2. The process of claim 1 further comprising freeing the separated oxalate from other precipitated heavy metal oxalates by washing with water.

3. The process of claim 1 wherein the solutions are in aliphatic carboxylic acids having a water content of more than 1% by weight.

4. The process of claim 3 wherein solutions in aliphatic carboxylic acids have a water content of more than 2% by weight.

5. The process of claim 4 wherein the solutions in aliphatic carboxylic acids have a water content of 5 to 10% by weight.

6. The process of claim 1 wherein the temperature ranges from about 80° to 160° C.

7. The process of claim 6 wherein 1 to 4 moles of oxalic ester are used per mole of the total amount of cobalt and/or manganese oxalate that is to be precipitated.

8. The process of claim 7, wherein 1.1 to 1.5 moles of oxalic ester are used.

9. The process of claim 1 wherein 1 to 4 moles of oxalic ester are used per mole of the total amount of cobalt and/or manganese oxalate that is to be precipitated.

10. The process of claim 9 wherein 1.1 to 1.5 moles of oxalic ester are used.

11. The process of claim 10 wherein oxalic acid dimethyl ester or oxalic acid diethyl ester is used.

12. The process of claim 1 wherein oxalic acid dimethyl ester or oxalic acid diethyl ester is used.

13. The process of claim 1 wherein the solution of cobalt and/or manganese to be treated is the mother liquors or reaction solutions from processes for the preparation of aromatic carboxylic acids by oxidation of alkyl aromatics in the presence of an aliphatic monocarboxylic acid as solvent and of cobalt and/or manganese catalyst.

14. The process of claim 1 wherein the solution of cobalt and/or manganese to be treated is the acetic acid extracts of distillation residues from processes for the preparation of dimethyl terephthalate by common air oxidation of p-xylene and p-toluylic acid methyl ester in liquid phase, esterification of the oxidate with methanol, and distillative separation of the esterification mixture.

* * * * *